(12) United States Patent
Agnello et al.

(10) Patent No.: US 12,183,459 B2
(45) Date of Patent: *Dec. 31, 2024

(54) DATA STORAGE AND RETRIEVAL SYSTEM FOR NON-CONTIGUOUS MEDICAL DEVICE

(71) Applicant: ABIOMED, Inc., Danvers, MA (US)

(72) Inventors: Alessandro Simone Agnello, Danvers, MA (US); Paul Roland Lemay, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/140,673

(22) Filed: Apr. 28, 2023

(65) Prior Publication Data

US 2023/0386658 A1 Nov. 30, 2023

Related U.S. Application Data

(63) Continuation of application No. 17/398,303, filed on Aug. 10, 2021, now Pat. No. 11,676,718, which is a
(Continued)

(51) Int. Cl.
*G16H 40/67* (2018.01)
*G06F 16/41* (2019.01)

(52) U.S. Cl.
CPC ............. *G16H 40/67* (2018.01); *G06F 16/41* (2019.01)

(58) Field of Classification Search
CPC ................................. G16H 40/67; G06F 16/41
See application file for complete search history.

(56) References Cited

U.S. PATENT DOCUMENTS 8,233,768 B2 7/2012 Soroushian et al.
2006/0085518 A1* 4/2006 Blackmore ............. H04L 67/10
709/217
(Continued)

FOREIGN PATENT DOCUMENTS

CN 101075467 A 11/2007
CN 101351845 A 1/2009
(Continued)

OTHER PUBLICATIONS

Alessandro Testa et al., Chapter 30. Services and Monitors for Dependability Assessment of Mobile Health Monitoring Systems, Services and Monitors for Dependability Assessment of Mobile Health Monitoring Systems (Dec. 31, 2016) (Year: 2016).*
(Continued)

*Primary Examiner* — Jordan L Jackson
(74) *Attorney, Agent, or Firm* — Botos Churchill IP Law LLP

(57) ABSTRACT

A web-based interface enables medical personnel to remotely monitor medical devices. A monitoring system records operational data and alarms from the medical devices in a file. However, since network connections between the medical devices and the monitoring system are intermittent, the file does not contain a contiguous stream of data for each medical device. The file pauses recording during gaps in network connectivity. The system displays current data, as well as a list of alarms. If medical personnel wish to view more detail about an earlier time or one of the alarms, the system calculates where in the file the medical device data was recorded. This calculation accounts for the discontiguous nature of the data. The system uses times the network connection is made and broken to calculate an index into the file that corresponds to the time of the user-selected alarm.

20 Claims, 13 Drawing Sheets

Related U.S. Application Data continuation of application No. 16/137,053, filed on Sep. 20, 2018, now Pat. No. 11,120,908.

(56) References Cited

U.S. PATENT DOCUMENTS

| | | |
|---|---|---|
| 2007/0280516 A1 | 12/2007 | Yoneyama et al. |
| 2009/0063187 A1 | 3/2009 | Johnson et al. |
| 2009/0063193 A1* | 3/2009 | Barton .................. G08B 21/02 340/539.11 |
| 2009/0238539 A1 | 9/2009 | Isobe et al. |
| 2009/0282162 A1* | 11/2009 | Mehrotra .............. H04L 65/752 709/233 |
| 2015/0317751 A1 | 11/2015 | Kalyvas et al. |
| 2018/0006831 A1 | 1/2018 | Toll et al. |

FOREIGN PATENT DOCUMENTS

| | | |
|---|---|---|
| CN | 103415852 A | 11/2013 |
| CN | 104301360 A | 1/2015 |
| CN | 104394380 A | 3/2015 |
| CN | 105306860 A | 2/2016 |
| JP | 2011502369 A | 1/2011 |
| JP | 2011523473 A | 8/2011 |
| JP | 2014199581 A | 10/2014 |
| JP | 2016005238 A | 1/2016 |
| JP | 2017202058 A | 11/2017 |
| JP | 2017204248 A | 11/2017 |
| JP | 2018501533 A | 1/2018 |
| KR | 20070009727 A | 1/2007 |
| KR | 20100106327 A | 10/2010 |
| WO | 2009120909 A1 | 10/2009 |
| WO | 2012118639 A2 | 9/2012 |
| WO | 2016057416 A1 | 4/2016 |

OTHER PUBLICATIONS

Office Action from corresponding Chinese Patent Application No. 2018800978608 dated Oct. 31, 2023. (13 pp.).

Halvorsen et al., "Storage Systems Support for Multimedia Applications", Research Report No. 307, Dept. of Informatics, University of Oslo, Norway, Jul. 12, 2006, 18 pages.

International Search Report—International Application No. PCT/US2018/066483, dated May 21, 2019, together with the Written Opinion of the International Searching Authority, 19 pages.

Office Action from corresponding Indian Patent Application No. 202117011840 dated Jan. 12, 2023 (8 pages).

Office Action from corresponding Japanese Patent Application No. 2021-515562 dated Mar. 1, 2023 (9 pages).

PCT Notification Concerning Transmittal of International Preliminary Report on Patentability, and PCT Written Opinion of the International Searching Authority issued in PCT application No. PCT/US2018/066483 on Apr. 1, 2021.

Shenoy et al., "Chapter 10. Multimedia Storage Servers", In Readings in Multimedia Computing and Networking, Elsevier Science & Technology, Aug. 10, 2001, pp. 655-716.

Testa et al., "Chapter 30. Services and Monitors for Dependability Assessment of Mobile Health Monitoring Systems", E-Health and Telemedicine: Concepts, Methodologies, Tools, and Applications, vol. II, Dec. 31, 2016, pp. 602-618.

Office Action from corresponding Australian Patent Application No. 2018442000 dated Apr. 30, 2024 (3 pp.).

Office Action issued in corresponding Canadian Patent Application No. 3,110,461, mailed Mar. 22, 2024, 7 pages.

* cited by examiner

Network Connectivity Log 1100

| Device ID 1102 | Time 1104 | Event (Connect, Disconnect) 1106 | File 1108 |
|---|---|---|---|
| IC2958 | 2018-9-10 2:01 | Connect | Archive2 |
| IC2958 | 2018-9-10 4:37 | Disconnect | Archive2 |
| IC2958 | 2018-9-10 4:39 | Connect | Archive2 |
| IC2958 | 2018-9-10 5:41 | Disconnect | Archive2 |
| IC2958 | 2018-9-10 5:42 | Connect | Archive2 |
| IC2958 | 2018-9-10 7:07 | Disconnect | Archive2 |
| IC2958 | 2018-9-10 7:12 | Connect | Archive2 |
| IC2958 | 2018-9-10 7:13 | Disconnect | Archive2 |
| IC2958 | 2018-9-10 7:45 | Connect | Archive2 |
| IC2958 | 2018-9-10 8:01 | Disconnect | Archive2 |
| IC2958 | 2018-9-10 8:05 | Connect | Media |
| IC2958 | 2018-9-10 8:37 | Disconnect | Media |
| IC2958 | 2018-9-10 11:45 | Connect | Media |
| IC2958 | 2018-9-10 12:01 | Disconnect | Media |
| IC2958 | 2018-9-10 12:32 | Connect | Media |
| IC2958 | 2018-9-10 12:51 | Disconnect | Media |
| IC2958 | 2018-9-10 13:07 | Connect | Media |
| IC2958 | 2018-9-10 14:20 | Disconnect | Media |
| IC2958 | 2018-9-10 14:33 | Connect | Media |
| IC2958 | 2018-9-10 14:59 | Disconnect | Media |
| ... | ... | ... | ... |

DATA STORAGE AND RETRIEVAL SYSTEM FOR NON-CONTIGUOUS MEDICAL DEVICE

CROSS-REFERENCE TO RELATED APPLICATIONS

The present application is a continuation of U.S. patent application Ser. No. 17/398,303, filed Aug. 10, 2021, now U.S. Patent No. 11,676,718, issued on Jun. 13, 2023, which application is a continuation of U.S. patent application Ser. No. 16/137,053, filed Sep. 20, 2018, now U.S. Pat. No. 11,120,908, issued on Sep. 14, 2021, the disclosures of which are incorporated herein by reference.

BACKGROUND OF THE INVENTION

The present invention relates to data storage and retrieval systems and, more particularly, to data storage and retrieval systems for collecting, storing and retrieving operational data about medical devices, where network connections over which the operational data are sent are intermittent, i.e., subject to occasional gaps in computer network connectivity.

RELATED ART

Many medical devices, such as some implanted heart pumps, should be monitored by medical personnel to ensure efficacy and patient safety. Some such medical devices have associated controllers that collect and display operational data about the medical devices, such as heart signal level, battery temperature and plumbing integrity. Some of these controllers raise alarms when operational data values fall beyond predetermined values or ranges, for example if a leak or loss of suction is detected. Many of these controllers include video display screens as human interfaces, on which the operational data and/or alarms are displayed.

In many cases, these medical devices are monitored remotely, especially in cases of ambulatory patients. In these cases, the controllers may be coupled via computer networks, often including wireless segments, to central servers, which may be accessed by monitoring stations. The monitoring stations may display real-time operational data and/or alarms on display screens for viewing by medical personnel. Typically, the servers also record the operational data, so operational data from earlier times can be "played back" upon request by the medical personnel.

However, computer network connections between the medical device controllers and the servers are often intermittent, i.e., subject to occasional gaps in computer network connectivity between the medical device controllers and the servers, particularly when the computer networks include wireless segments. The medical device controllers typically lack sufficient memory to store operational data during these gaps, or the device controllers lack an ability to detect these gaps. Thus, the medical device controllers cannot compensate for these gaps by transmitting operational data from earlier times, once a network connection is restored. Instead, the medical device controllers simply transmit their current operational data whenever computer network connections to the servers exist. Therefore, the operation data recorded by the servers often include gaps, corresponding to the gaps in computer network connectivity.

The servers record the operational data, as and when the operational data is received from the medical device controllers. However, during gaps in computer network connectivity, the servers pause recording, because the servers have nothing to record. Consequently, although recorded operational data is stored in contiguous data files, the stored data does not represent continuous time, which has made it impossible to index into a data file to a time of interest. Instead, in the prior art, medical personnel are limited to playing back the recorded operational data from the beginning of a data file, or guessing how far to index into the data file to find operational data that corresponds to the time of interest.

SUMMARY OF EMBODIMENTS

An embodiment of the present invention provides a data storage and retrieval system for non-contiguous medical device data. The system includes a medical device. The medical device is connectable to a computer network. The medical device is subject to occasional gaps in connectivity to the computer network. The medical device is configured to automatically repeatedly capture status information about the medical device and send messages containing the status information via the computer network.

The system also includes a network connectivity log. The network connectivity log is configured to automatically record times at which the medical device connects to the computer network. The network connectivity log is also configured to automatically record times at which the medical device disconnects from the computer network.

The system also includes a data store. The data store is configured to automatically store digital media data in a media file. The data store is also configured to automatically provide a requested portion, less than all, of the stored media file in response to a provision request. The provision request includes an index, relative to an end of the media file, that corresponds to the requested portion.

The system also includes a media server. The media server is connectable to the computer network. The media server is configured to automatically receive the messages via the computer network. The media server is also configured to automatically store status information from received messages into the data store. Status information from consecutive received messages is stored contiguously in the data store, notwithstanding the occasional gaps in connectivity between the medical device and the computer network.

The media server is also configured to automatically receive a status request that includes a time at which requested status information was captured. The media server is also configured to automatically access the network connectivity log and calculate an index, relative to an end of the media file, where the requested status information is stored. In performing this calculation, the media server is configured to take into account the occasional gaps in connectivity between the medical device and the computer network as represented in the network connectivity log.

The media server is also configured to automatically request a portion of the stored media file beginning at the calculated index. The media server is further configured to automatically provide the portion of the stored media file beginning at the calculated index.

In any embodiment, the data store may be further configured to store digital media data in at least one archive file. When the media file stores a predetermined amount of digital media data, the digital media data stored in the media file may be copied to the at least one archive file. In any embodiment, the data store may be configured to provide a requested portion, less than all, of the stored archive file in response to a provision request. The provision request may include an index, relative to an end of the archive file, that corresponds to the requested portion.

In any embodiment, the network connectivity log may be further configured to automatically record, for each period of connectivity to the computer network, information identifying one of the media file and the archive file where the digital media data is stored.

In any embodiment, the media server may be further configured to access the network connectivity log and calculate an index, relative to an end of the archive file, where the requested status information is stored. The calculation may take into account the occasional gaps in connectivity between the medical device and the computer network as represented in the network connectivity log.

In any embodiment, the media server may be further configured to request a portion of the stored archive file beginning at the calculated index. In any embodiment, the media server may be further configured to provide the portion of the stored archive file beginning at the calculated index.

In any embodiment, the media server may be further configured to automatically cause display of a pop-up message when a message indicates the medical device requires attention.

In any embodiment, the pop-up message may include a URL of a web page that contains additional information about the status of the medical device.

Any embodiment may also include an outgoing e-mail server configured to send an e-mail message when a message from the medical device indicates the medical device requires attention.

In any embodiment, the e-mail message may include a URL of a web page that contains additional information about the status of the medical device.

Another embodiment of the present invention provides a method for storing and retrieving non-contiguous medical device data. The method includes connecting a medical device to a computer network, subject to occasional gaps in connectivity to the computer network. The method further includes automatically repeatedly capturing, by the medical device, status information about the medical device and sending, by the medical device, messages containing the status information via the computer network. The method further includes automatically recording in a network connectivity log (a) times at which the medical device connects to the computer network and (b) times at which the medical device disconnects from the computer network.

The method further includes storing, in a data store, digital media data in a media file. The method further includes providing, by the data store, a requested portion, less than all, of the stored media file in response to a provision request. The provision request includes an index, relative to an end of the media file, that corresponds to the requested portion.

The method further includes receiving, by a media server, the messages via the computer network. The method further includes storing, by the media server, status information from received messages into the data store. Status information from consecutive received messages is stored contiguously in the data store, notwithstanding the occasional gaps in connectivity between the medical device and the computer network.

The method further includes receiving, by the media server, a status request that includes a time at which requested status information was captured. The method further includes accessing, by the media server, the network connectivity log and calculating an index, relative to an end of the media file. The requested status information is stored, taking into account the occasional gaps in connectivity between the medical device and the computer network as represented in the network connectivity log. The method further includes requesting, by the media server, a portion of the stored media file beginning at the calculated index. The method further includes providing, by the media server, the portion of the stored media file beginning at the calculated index.

In any embodiment, the method may further include storing digital media data in at least one archive file and, when the media file stores a predetermined amount of digital media data, copying the digital media data stored in the media file to the at least one archive file. A requested portion, less than all, of the stored archive file may be provided in response to a provision request. The provision request may include an index, relative to an end of the archive file, that corresponds to the requested portion. For each period of connectivity to the computer network, information identifying one of the media file and the archive file where the digital media data is stored may be automatically recorded in the network connectivity log.

In any embodiment, the network connectivity log may be accessed by the media server and an index may be calculated, relative to an end of the archive file, where the requested status information is stored, taking into account the occasional gaps in connectivity between the medical device and the computer network as represented in the network connectivity log.

In any embodiment, a portion of the stored archive file beginning at the calculated index may be requested by the media server. The portion of the stored archive file beginning at the calculated index may be provided by the media server.

In any embodiment, the method may further include automatically causing, by the media server, display of a pop-up message when a message indicates the medical device requires attention.

In any embodiment, the pop-up message may include a URL of a web page that contains additional information about the status of the medical device.

In any embodiment, the method may further include automatically sending, by an outgoing e-mail server, an e-mail message when a message from the medical device indicates the medical device requires attention.

In any embodiment, the e-mail message may include a URL of a web page that contains additional information about the status of the medical device.

Yet another embodiment of the present invention includes a non-transitory computer-readable medium encoded with instructions. When executed by a processor, the instructions establish processes for performing a computer-implemented method for storing and retrieving non-contiguous medical device data. The processes include a process configured to connect a medical device to a computer network, subject to occasional gaps in connectivity to the computer network. A process is configured to automatically repeatedly capture, by the medical device, status information about the medical device and send, by the medical device, messages containing the status information via the computer network. A process is configured to automatically record in a network connectivity log (a) times at which the medical device connects to the computer network and (b) times at which the medical device disconnects from the computer network.

A process is configured to store, in a data store, digital media data in a media file. A process is configured to provide, by the data store, a requested portion, less than all, of the stored media file in response to a provision request, wherein the provision request includes an index, relative to an end of the media file, that corresponds to the requested portion.

A process is configured to receive, by a media server, the messages via the computer network. A process is configured to store, by the media server, status information from received messages into the data store, wherein status information from consecutive received messages is stored contiguously in the data store, notwithstanding the occasional gaps in connectivity between the medical device and the computer network. A process is configured to receive, by the media server, a status request that includes a time at which requested status information was captured.

A process is configured to access, by the media server, the network connectivity log and calculate an index, relative to an end of the media file, where the requested status information is stored, taking into account the occasional gaps in connectivity between the medical device and the computer network as represented in the network connectivity log. A process is configured to request, by the media server, a portion of the stored media file beginning at the calculated index. A process is configured to provide, by the media server, the portion of the stored media file beginning at the calculated index.

BRIEF DESCRIPTION OF THE DRAWINGS

The invention will be more fully understood by referring to the following Detailed Description of Specific Embodiments in conjunction with the Drawings, of which:

FIG. 7 is an exemplary hypothetical web page generated by the data storage and retrieval system of FIG. 1 and listing medical devices that may be selected for monitoring, according to an embodiment of the present invention.

FIG. 11 is a schematic diagram illustrating data fields of a network connectivity log of FIG. 1, according to an embodiment of the present invention.

DETAILED DESCRIPTION OF SPECIFIC EMBODIMENTS

Figure 1:
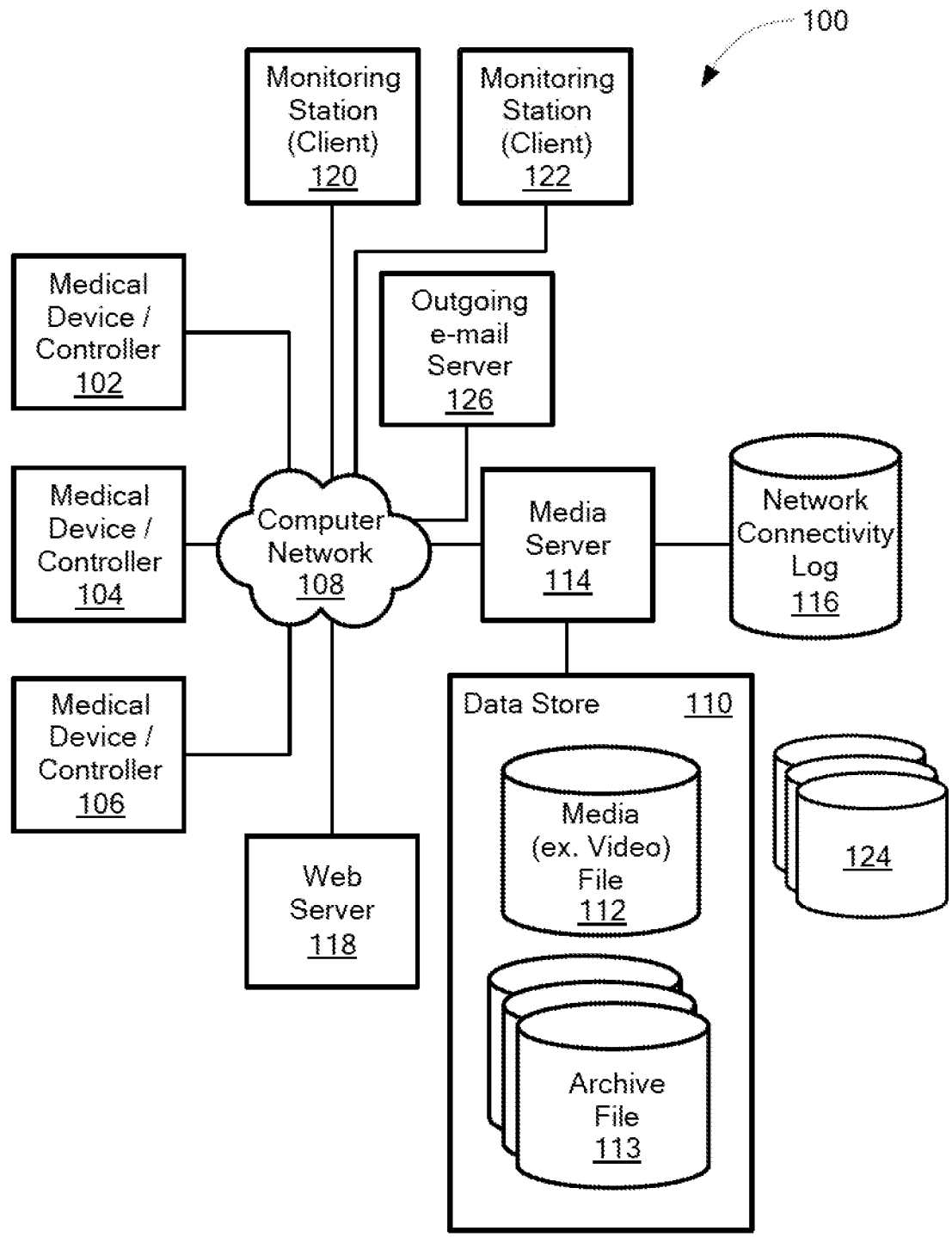
FIG. 1 is a schematic block diagram of major components of a data storage and retrieval system for collecting, storing and retrieving operational data about medical devices, according to an embodiment of the present invention.

Embodiments of the present invention provide data storage and retrieval systems and methods for non-contiguous medical device operational data. A web-based interface enables medical personnel to remotely monitor medical devices, such as implanted heart pumps. A monitoring system records operational data, such as battery temperature and alarms from the medical devices, in a file. However, since network connections between the medical devices and the monitoring system are intermittent, the file does not contain a contiguous stream of data for each medical device. Instead, the file simply records data when data is available. The file pauses recording during gaps in the data, i.e., during gaps in network connectivity. The file may be in the form of a video file, such as an MP4 file, although other suitable file formats may be used.

The system displays current, or most recently available, data, as well as a list of alarms. If medical personnel wish to view more detail about an earlier time or one of the alarms, the system calculates where in the file the medical device data was recorded. This calculation is novel and not obvious, due to the discontiguous nature of the data. For each medical device, the system records times the medical device connects via the network ("network connect events") and times the medical device network connection breaks ("network disconnect events"). The system uses these times to calculate an index into the file that corresponds to the time of the user-selected alarm.

Optionally, the system notifies users of alarms by sending e-mail messages and/or text messages and/or by displaying pop-up windows in browsers. The messages or pop-up windows may include links, such as URLs, to web pages that display information about the alarms. Users may click on the URL to open the web pages.

Definitions

Unless otherwise indicated, the following terms, as used herein, shall have the following meanings.

Contiguous—sharing a common border, touching. Data, such as records, blocks, video frames, etc., that are stored contiguously are stored without space between consecutive elements.

Discontiguous—not contiguous; not sharing a common border; not touching. Data, such as records, blocks, video frames, messages, etc., that are stored discontiguously have space between consecutive elements. Data, such as records, blocks, video frames, messages, etc., that are received discontiguously have missing elements between consecutive received elements.

Continuous—forming an unbroken whole, without interruption.

Connect to a computer network—establish or reestablish a connection to the computer network, without necessarily establishing a new network session.

Disconnect from a computer network—lose, including temporarily, a connection to the computer network. For example, in a wireless computer network link, electrical noise, a strong signal from another station, a change in propagation characteristics, such as due to movement or change in orientation of an antenna, or interposition, between a transmitting antenna and a receiving antenna, of a material that attenuates or reflects electromagnetic waves, may temporarily cause loss of connectivity.

Digital media data—digital data that represent imagery, video and/or sound.

Consecutive—one element after another like element, without a third element between. For example, with two consecutive messages, one message follows the other, without a third message in between, although there may be a gap in time between the two messages.

Time—a time may include a date and a time within the date, for example 2018-9-12 3:52.

Major Components

FIG. 1 is a schematic block diagram of major components of a data storage and retrieval system 100 for collecting, storing and retrieving operational data from and about medical devices, represented by exemplary medical devices 102, 104 and 106. Although three medical devices 102-106 are shown, other numbers of medical devices may be used. Each medical device 102-106 is connectable to a computer network 108. Each medical device 102-106 is configured to automatically repeatedly capture status information about the medical device 102-106 and send messages containing the status information via the computer network 108. In some embodiments, the status information is sent in the messages encoded as a video frame or a sequence of video frames. The video frame(s) may, for example, contain copies of images displayed on display screens of the medical devices 102-106.

The computer network 108 may include wired and/or wireless segments. Each medical device 102-106 is, therefore, subject to occasional gaps in connectivity to or through the computer network 108.

A data store 110 includes a media file 112, such as an MP4 video or other suitable type of media file. As described in more detail below, the data store 110 records the status information about the medical devices 102-106. The data store 110 is configured to automatically store digital media data, such as frames of video, in the media file 112.

The data store 110 is also configured to provide a requested portion, less than all, of the stored media file 112 in response to a provision request. The data store 110 thereby supports playback of the medical device status information, as described in more detail below. For example, the data store 110 may provide one or more frames of video stored in the media file 112, for display to a user.

Such a provision request includes an index, relative to the beginning or the end of the media file 112. The index corresponds to the beginning of the requested portion, i.e., how far into the media file 112 the data store 110 must seek to reach the beginning of the requested portion. For example, the index may indicate an amount of time, or a number of video frames, from the beginning or the end of the media file 112 to where the requested portion begins. For example, a provision request may request a video frame that begins 7 minutes and seconds (7:15) from the beginning of the media file 112. In another example, a provision request may request a sequence of video frames that begins 3,872 frames from the end of the media file 112.

Optionally, the data store 110 is configured to create and maintain one or more archive files, represented by archive file 113. Although three archive files 113 are shown, any number of archive files 113 may be used. In some embodiments that are configured to maintain the archive files 113, when the media file 112 reaches a predetermined size, such as about five hours' worth of status information, the data store 110 makes an archive copy 113 of the media file 112 and begins recording from the beginning of the media file 112, thereby overwriting previously stored status information in the media file 112. In some embodiments, after the media file 112 reaches the predetermined size, the data store 110 closes the media file 112, renames the media file 112 to the next available archive file 113 name and creates a new media file 112. Copying the contents of the media file 112 into the archive file 113 and closing and renaming the media file 112 to the next available archive file 113 are collectively herein referred to as copying the digital media data stored in the media file to the at least one archive file.

A media server 114 is connectable to the computer network 108 and is configured to automatically receive, via the computer network 108, the messages containing the status information from the medical devices 102-106. The media server 114 may parse the messages to extract the status information from the messages. For example, in some embodiments, the media server 114 includes an optical character recognizer (OCR) to recognize text in video frames sent by the medical devices 102-106. In some embodiments, the media server 114 is communicably coupled to a separate OCR (not shown).

The media server 114 may then use the recognized text to automatically ascertain serial numbers or other identifiers of the medical devices 102-106, operating parameters of the medical device 102-106, whether an alarm has been raised by one of the medical devices 102-106, etc. The media server 114 is further configured to store the status information from received messages into the data store 110, typically in the form of video frames. In addition, as described below, the media server 114 facilitates playing back (displaying to a user) requested portions of the recorded medical device status information.

The media server 114 stores received status information into the data store 110 as the media server 114 receives the status information. However, the media server 114 does not receive messages from a given medical device 102-106 during the occasional gaps in connectivity to the computer network 108 experienced by the medical device 102-106. The media server 114 pauses storing status information about the given medical device 102-106 into the data store 110 during each gap in network connectivity. Thus, status information from consecutive received messages may be stored contiguously in the data store, even if there is a time gap, represented by a network connectivity gap, between the consecutive received messages. Consequently, contiguous data in the media file 112 does not necessarily represent continuous time, i.e., status information continuously collected by a medical device 102-106.

The status information from consecutive received messages is stored contiguously in the data store, notwithstanding the occasional gaps in connectivity between the medical device 102-106 and the computer network 108. Additional components, which are described below, solve the problem of correctly indexing into the media file 112 to retrieve status information associated with a requested time, i.e., accounting for the non-contiguous nature of the status information conveyed by the received messages.

A network connectivity log 116 is configured to automatically record: (a) times at which each medical device 102-106 connects to the computer network 108 and (b) times at which each medical device 102-106 disconnects from the computer network 108. A time at which a first message is received by the media server 114 from a given medical device 102-106 may be taken as the time the medical device 102-106 connects to the computer network 108. If no message has been received by the media server 114 from a given medical device 102-106 for a predetermined timeout period, the medical device 102-106 may be assumed to have lost network connectivity, and the time at which the timeout is detected, minus the timeout period, may be taken as the time the medical device 102-106 disconnected from the computer network 108.

After such a disconnect event, if a message is received by the media server 114 from the medical device 102-106, the medical device 102-106 may be assumed to have again connected to the computer network 108, and a time at which the message is received by the media server 114 from the given medical device 102-106 may be taken as the time the medical device 102-106 reconnects to the computer network 108.

In some embodiments, the medical devices 102-106 periodically transmit or broadcast messages, without necessarily including any device status information. These messages are sent to indicate the respective medical devices 102-106 are operational. Receipt of these messages indicates the respective sending medical device 102-106 is connected, via the computer network 108, to the recipient. Therefore, a cessation of receipt of these messages may be used as an indication the respective medical device 102-106 has lost computer network connectivity, i.e., the beginning of a gap in computer network connectivity. A time of this loss may be stored in the network connectivity log 116.

If one of these messages is subsequently received, the respective medical device 102-106 may be assumed to again be connected to the computer network 108, and a time of this reconnection may be stored in the network connectivity log 116. More detailed descriptions of several embodiments of the network connectivity log 116 are provided herein.

All the messages from a given medical device 102-106 to the media server 114 may be carried over a single network session, despite gaps in the network connectivity. Alternatively, each or some of the gaps may cause termination of a network session, and resumption of network connectivity may cause creation of a new network session.

Figure 2:
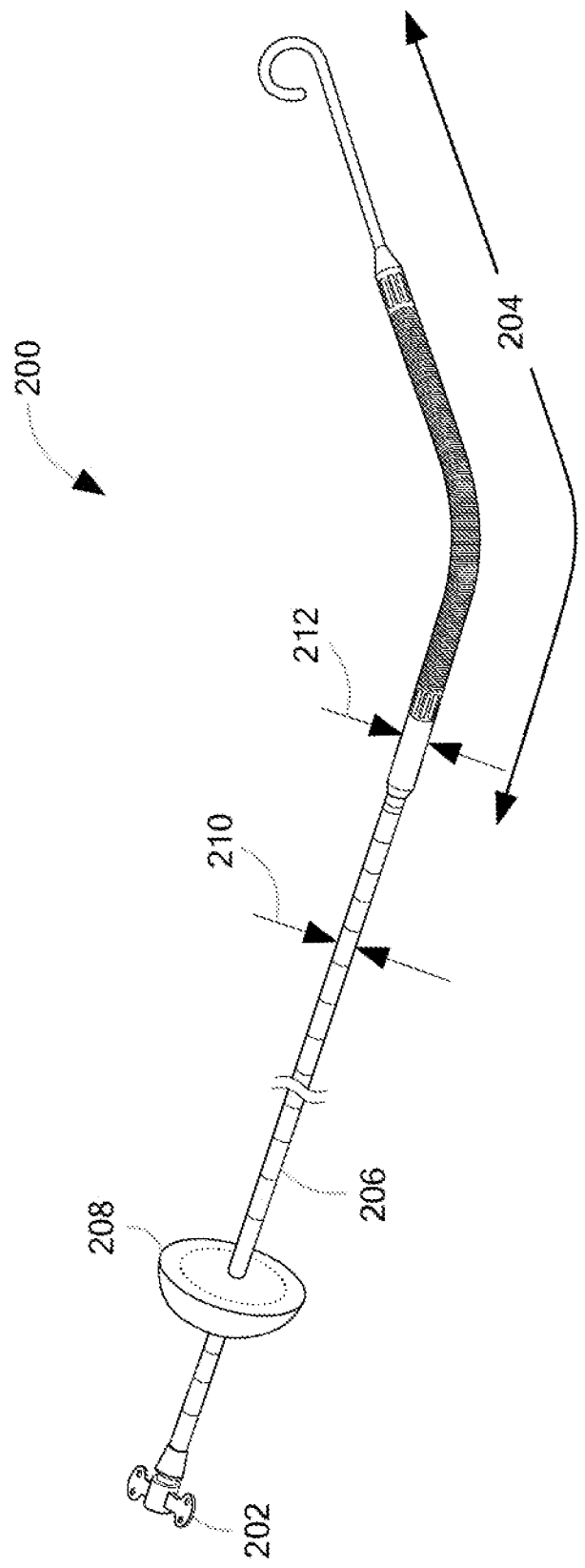
FIG. 2 is an isometric view of an exemplary medical device that may be included in the system of FIG. 1.

FIG. 2 is an isometric view of an exemplary medical device 200. The exemplary medical device 200 is an intravascular blood pump. However, many other kinds of suitable medical devices may be used as each of the medical devices 102-106 in FIG. 1. The pump 200 includes a pump handle 202, a pump head 204, a catheter 206 connecting the pump handle 202 to the pump head 204, and a connecting hub 208. The catheter 206 is tubular and has a substantially uniform outer diameter 210. The catheter 206 enables the pump head 204 to be in electro-mechanical communication with the pump handle 202.

The pump handle 202 is in communication with control circuitry (described below), which allows control of the pump head 204. The pump head 204 contains electro-mechanical components that enable the device to perform various tasks within the body of a human patient, such as pump blood from a location within the body. The pump head 204 has a diameter 212 that is larger than the diameter 210 of the catheter 206. An example of such a percutaneous pump 200 is the Impella 2.5® blood pump system available from Abiomed, Inc., Danvers, Massachusetts. This blood pump system includes the pump 200 and an Automatic Impella Controller (AIC) controller for the pump 200.

Figure 3:
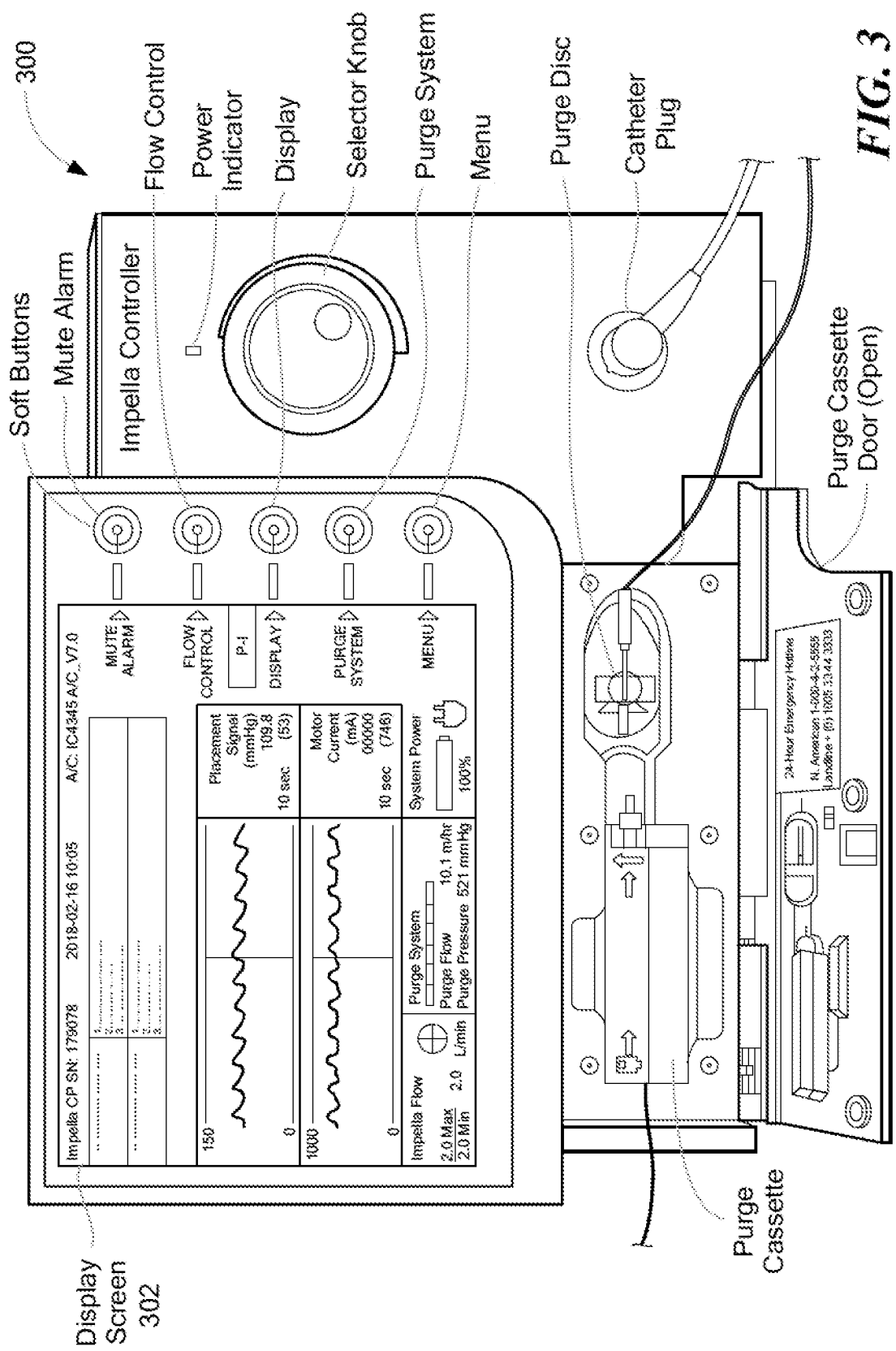
FIG. 3 is a front view of an exemplary medical device controller that may be coupled to the medical device of FIG. 2 and included in embodiments of the present invention.

FIG. 3 is a front view of an exemplary medical device controller 300, such as the above-mentioned Automatic Impella Controller (AIC) controller, that may be coupled to the medical device 200 of FIG. 2 and included in embodiments of the present invention. The medical device controller 300 provides a human interface for monitoring and controlling functions of the pump 200. The medical device controller 300 may include a display screen 302 that displays images of a video stream, in which the images illustrate data associated with the medical device 200 over time. In some implementations, the display screen 302 displays real-time operating and/or medical data associated with the pump 200.

Figure 4:
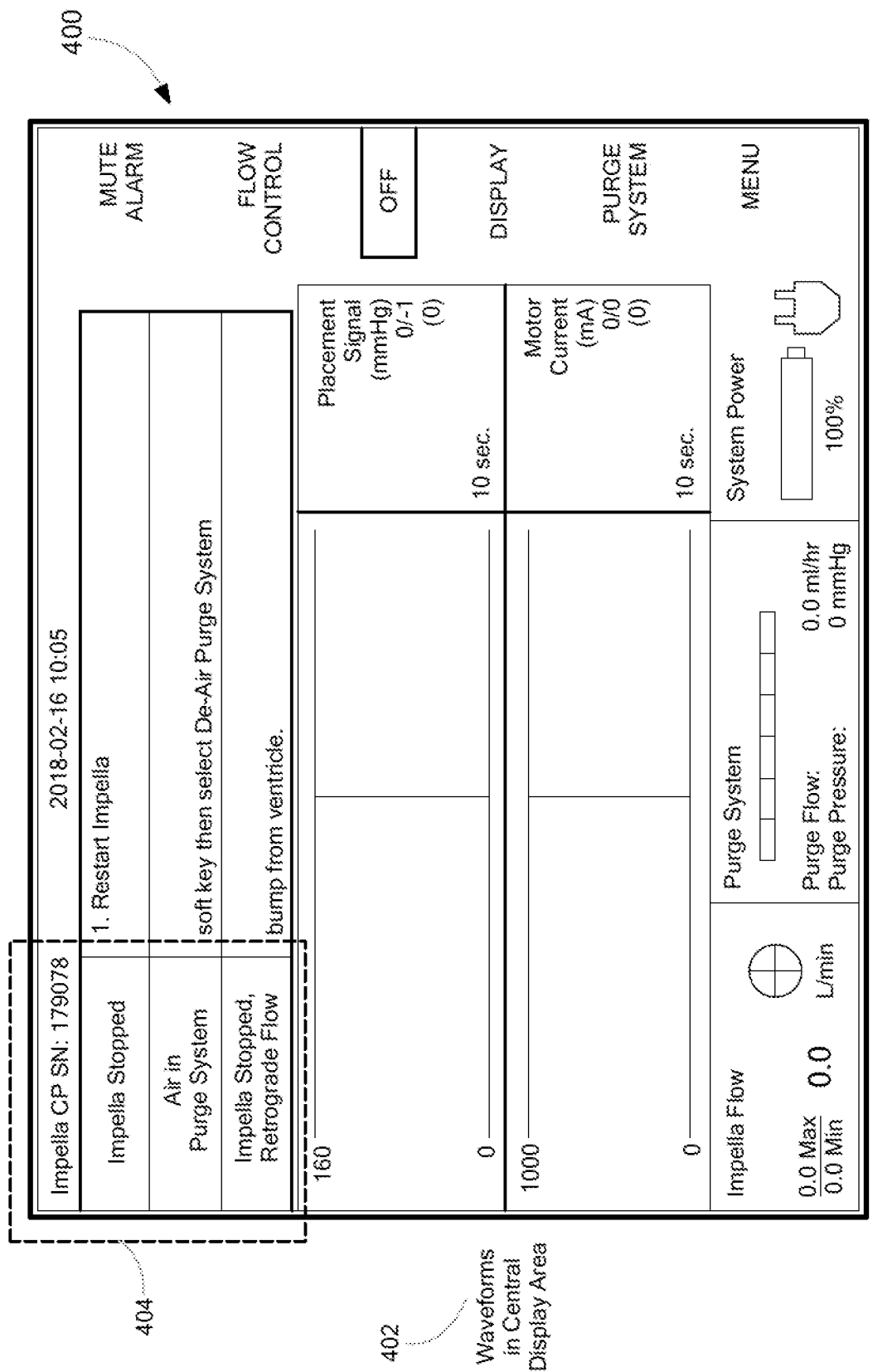
FIG. 4 is an exemplary hypothetical image displayed on a display screen of the medical device controller of FIG. 3.

FIG. 4 is an exemplary hypothetical image (frame) 400 displayed on the display screen 302 of the medical device controller 300 of FIG. 3. The image 400 may include waveforms 402 illustrating medical and/or operational data corresponding to operation of the corresponding pump 200. Examples of medical data illustrated by the waveforms 402 include placement signal and motor current. The waveforms 402, such as the motor current waveform, may provide a history, representation and/or illustration of motor current over a period time, for example 10 seconds. In this way, the image 400 includes motor current data, and possibly other data (collectively status information about the medical device 102-106), associated with the pump 200 over a period of time, such as 10 seconds.

Figure 5:
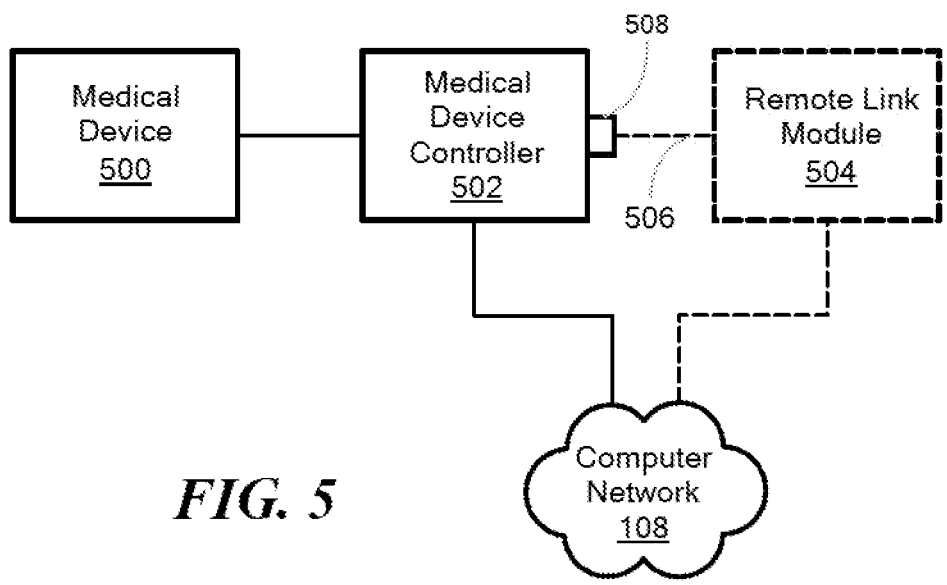
FIG. 5 is a schematic block diagram illustrating ways a medical device controller may be communicably coupled to a computer network, such as via a remote link module, according to the prior art.

As shown schematically in FIG. 5, a medical device 500 may be communicably coupled to an associated medical device controller 502, as discussed above. In some embodiments, the medical device controller 502 is directly communicably coupled to the computer network 108 and sends a stream of video frames, representing real time (current) contents of the display screen 302 (FIG. 3), via the computer network 108. Alternatively, the medical device controller 502 may periodically, such as every 20 seconds, or occasionally, capture a frame of the video representing the current contents of the display screen 302 and send that video frame.

However, some medical device controllers 502 are incapable of sending video frames via the computer network 108. In such cases, a remote link module 504 may be communicably coupled to the medical device controller 502, such as via a cable 506 connected to a video output port 508 of the medical device controller 502. The remote link module 504 may thereby receive a video signal representative of the contents of the display screen 302 (FIG. 3). The remote link module 504 may also be communicably coupled to the computer network 108.

The remote link module 504 may send a stream of video frames, representing real time (current) contents of the display screen 302 (FIG. 3), via the computer network 108. Alternatively, the remote link module 504 may periodically, such as every 20 seconds, or occasionally, capture a frame of the video representing the current contents of the display screen 302 and send that video frame. Additional information about the remote link module 504 is available in U.S. patent application Ser. No. 15/941,695, filed 30 Mar. 2018, assigned to the assignee of the present invention and titled "Systems and Methods for Capturing Data from a Medical Device," the entire contents of which are hereby incorporated by reference herein, for all purposes.

For simplicity of explanation, the medical device 200 (FIG. 2) or 500 (FIG. 5), its associated medical device controller 300 (FIG. 3) or 502 (FIG. 5) and, if used, its associated remote link module 504 (FIG. 5) are referred to herein collectively as one of the medical devices 102-106. As discussed with respect to FIG. 1, each medical device 102-106 is connectable to the computer network 108.

As noted, the media server 114 (FIG. 1) may include or use an optical character recognizer (OCR) that parses predefined regions of the video frames received from the medical devices 102-106, for example to convert text displayed in the video frames to computer character data, such as ASCII or UNICODE. For example, region 404 (FIG. 4) may be parsed by the OCR to extract the medical device serial number (SIN) and any error indicators, ex. "Impella Stopped," "Air In Purge System" and "Impella Stopped. Retrograde Flow." U.S. patent application Ser. No. 16/134,213, filed 18 Sep. 2018, assigned to the assignee of the present application and titled "Systems and Methods for Time-Based One-Time Password Management for a Medical Device," the entire contents of which are hereby incorporated by reference herein for all purposes, describes such an OCR mechanism.

Figure 6:
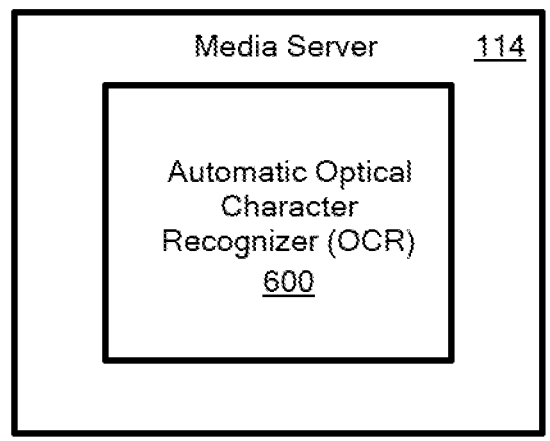
FIG. 6 is a schematic block diagram of a portion of an image feature extraction component, in this example an automatic optical character recognizer, used by a media server of the system of FIG. 1, according to the prior art.

FIG. 6 is a schematic block diagram of the media server 114, including an automatic optical character recognizer 600. However, as noted, the OCR may be a separate component. As noted, the media server 114 (FIG. 1) may recognize text in video frames sent by the medical devices 102-106 to automatically ascertain serial numbers or other identifiers of the medical devices 102-106, operating parameters of the medical device 102-106, whether an alarm has been raised by one of the medical devices 102-106, etc. In other embodiments, the medical device serial numbers or other identifiers, operating parameters, alarms, etc. may be encoded as metadata that accompany the video frame(s), and the media server 114 may access this metadata instead of, or in addition to, recognizing text in the video frame(s).

A web server 118 (FIG. 1), such as an HTTP server, serves web pages to clients, represented by monitoring stations (clients) 120 and 122. The monitoring stations 120 and 122 may be computers executing conventional web browsers. Although two monitoring stations 120-122 are shown, any number of monitoring stations may be included. The web server 118 communicates with the media server 114, such as to obtain a list of medical devices 102-106, for which status information is available live or for playback from the data store 110.

Figure 7:
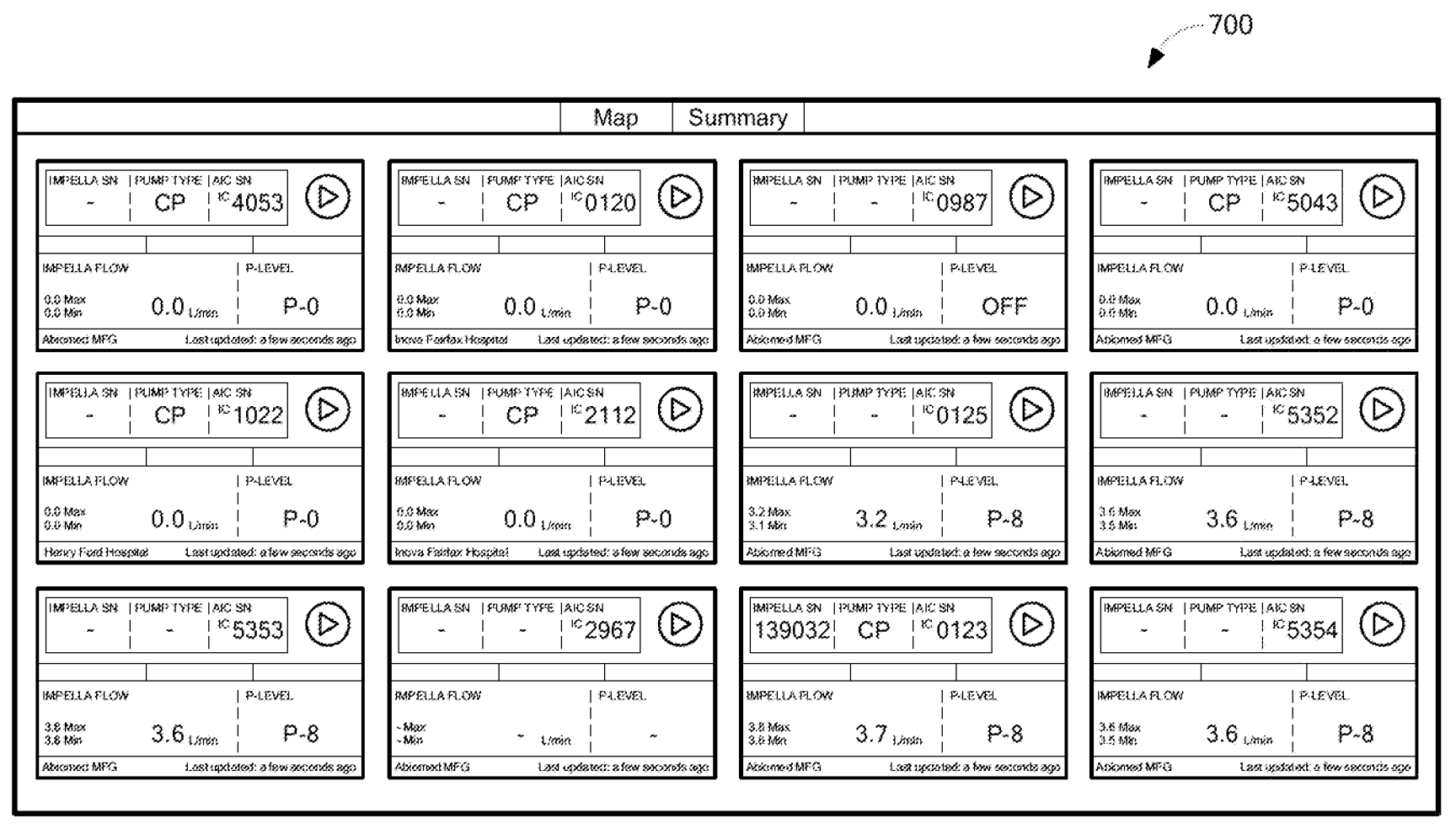

The web pages enable users of the monitoring stations 120-122 to select and then monitor individual medical devices 102-106. For example, a web page, exemplified by a web page 700 shown in FIG. 7, may display a list of available medical device 102-106 serial numbers or other identifiers, and the web page 700 may solicit a user to select one of the medical devices 102-106 to monitor, such as by clicking on one of the displayed medical device identifiers.

Figure 8:
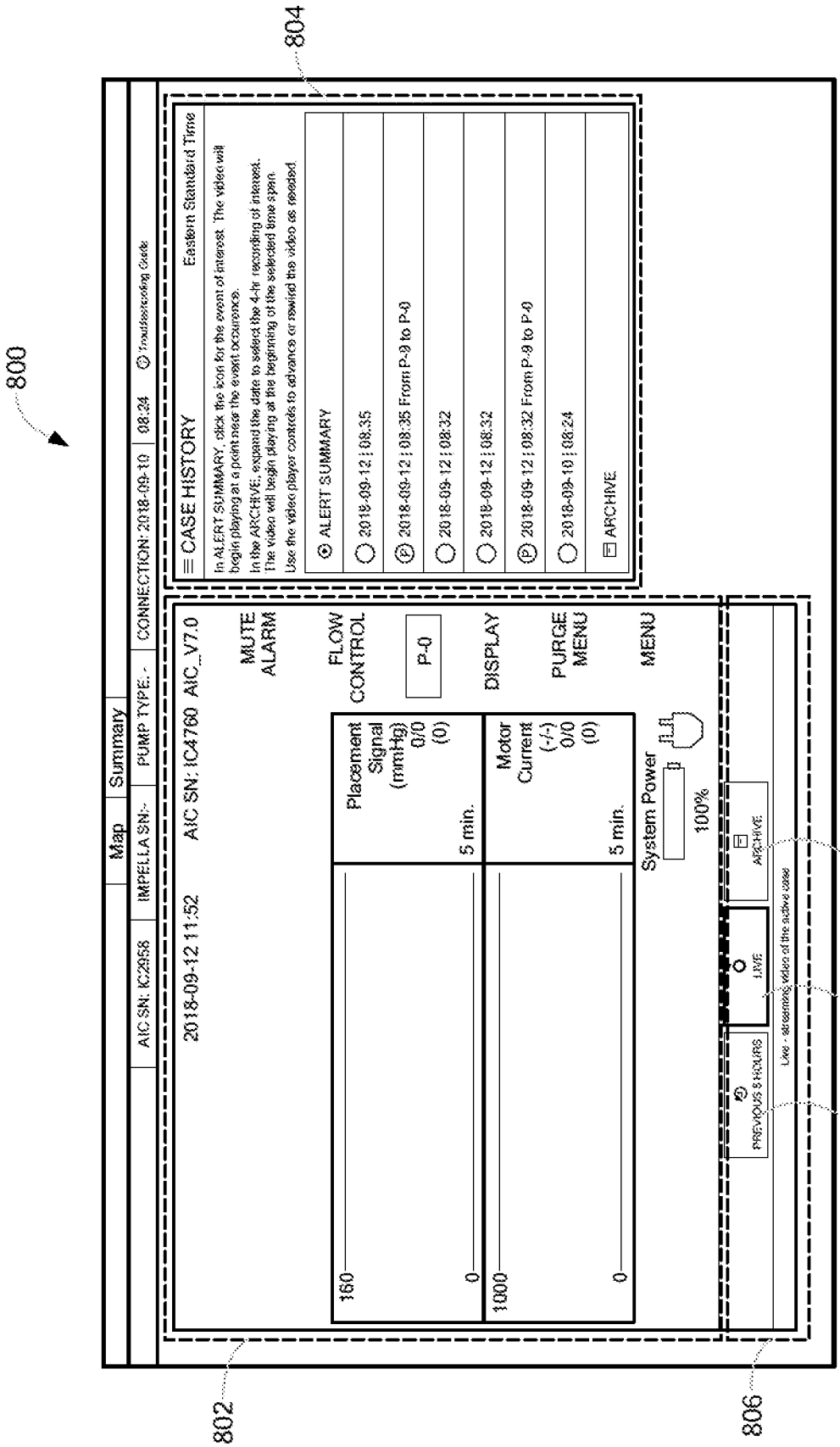
FIG. 8 is an exemplary hypothetical "live" web page display provided by a monitoring station (client device) of the data storage and retrieval system of FIG. 1, according to an embodiment of the present invention.

FIG. 8 illustrates an exemplary hypothetical web page 800 generated by the web server 118. The web page 800 displays "live" status information about one of the medical devices 102-106. A portion 802 of the web page 800 reproduces part or all of the imagery displayed on the corresponding medical device's controller screen 302 (FIG. 3). The web server 118 (FIG. 1) obtains video frames from the media server 114 to generate and update the web page 800, including the portion 802. In some embodiments, the web server 118 streams the video frames from the media server 114 to the monitoring station 120 or 122 for display in the portion 802.

As noted, the media server 114 may automatically ascertain whether an alarm has been raised by one of the medical devices 102-106. In addition, the media server 114 may analyze portions of the imagery from the medical devices 102-106 to automatically detect anomalies or other conditions that warrant attention, and/or the media server 114 may automatically detect undesirable conditions, such as sub-par computer network connectivity. Sub-par computer network connectivity may, for example, be declared if computer network connectivity, as measured by a percentage of "up" time, drops below a predetermined value, an excessive number gaps in computer network connectivity is detected, or an excessive total gap time over a predetermined period of time for a given medical device 102-106 is detected.

A portion 804 ("Alert Summary") of the web page 800 (FIG. 8) contains a list of alarms, warnings, anomalies, conditions that warrant attention, etc. Each such alert may be color coded according to urgency or significance. Each alert displays a time, at which the alert was generated or detected. Some alerts also display additional information. The alerts are listed in chronological order, with the most recent alert at the top of the list. If the portion 804 is insufficiently large to list all the alerts, older alerts may be hidden and made accessible via scroll elements (not shown) on the web page 800. A user clicking on one of the displayed alerts causes the web server 118 to replace the live portion 802 of the web page 800 with a reproduction of part or all of the imagery displayed on the corresponding medical device's controller screen 302 (FIG. 3) at the time of the alert, as described in more detail below.

A third portion 806 of the web page 800 (FIG. 8) includes buttons 808, 810 and 812 that enable a user to select among "Live" 810 view (described above), a previous time period, such as "Previous 5 Hours" 808, or an "Archive" 812 of recorded medical device status information. In some embodiments, the data store 110 (FIG. 1) records status information about each medical device 102-106 in the media file 112 for up to a fixed amount of time, such as about five hours, and thereafter makes an archive copy 113 of the media file 112 and begins recording in a new media file 112. Alternatively, the data store 110 renames the media file 112 as the next available archive file 113 and creates a new media file 112. In yet another embodiment, after the media file 112 is filled with the fixed amount of status information, such as about five hours' worth of data, as additional status information is received and recorded into the media file 112, a corresponding amount of the oldest data in the media file 112 is moved to an archive file 113. In this way, the media file 112 contains the most recent (in this example five hours) status information.

Figure 9:
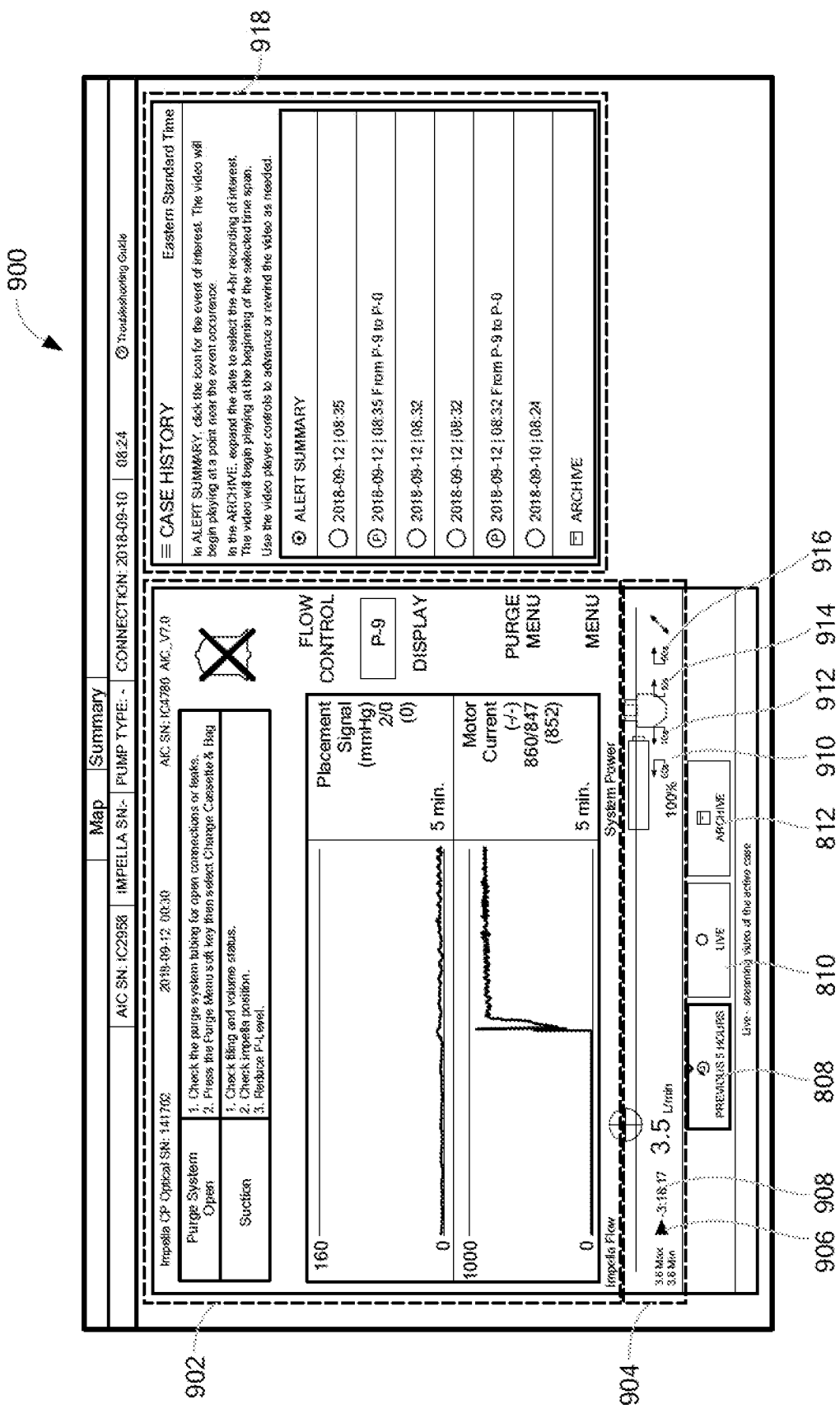
FIG. 9 is an exemplary hypothetical "previous five hours" web page display provided by a monitoring station (client device) of the data storage and retrieval system of FIG. 1, according to an embodiment of the present invention.

Clicking on the "Previous 5 Hours" button 808 causes the web server 118 to replace the live portion 802 of the web page 800 with a reproduction of part or all of the imagery displayed on the corresponding medical device's controller screen 302 (FIG. 3) earlier, up to five hours earlier, in time than the present time. FIG. 9 is an exemplary hypothetical web page 900 generated by the web server 118 to display previously recorded status information about one of the medical devices 102-106. As in the live display, a portion 902 of the web page 900 reproduces part or all of the imagery displayed on the corresponding medical device's controller screen 302 (FIG. 3), except from an earlier time.

Another portion 904 of the web page 900 includes user interface controls that enable a user to play/stop 906 the status information in the portion 902, view the time 908 at which the currently displayed 902 status information was received, back up (rewind) 60 seconds 910 from the currently displayed status information, back up (rewind) 10 seconds 912 from the currently displayed status information, skip forward (fast forward) 10 seconds 914 beyond the currently displayed status information and skip forward (fast forward) 60 seconds 916 beyond the currently displayed status information. In some embodiments, the time 908 may be entered by a user to specify a specific time at which playback is to begin.

A third region 918 of the web page 900 contains an Alert Summary and operates in a manner similar to the Alert Summary 804 described with respect to FIG. 8.

As noted, in some embodiments, the media file 112 (FIG. 1) contains only up to a predetermined amount of status information, such as about five hours' worth of status information, and older status information is stored in one of possibly many archive files 113. The "Archive" button 812 (FIGS. 8 and 9) enables a user to command playback of medical device status information from an archive file 113.

Although one media file 112 is shown in FIG. 1, for live monitoring the media file 112 may comprise several files, as indicated at 124. Multiple media files 124 may be used, particularly if simultaneous read and write access to a single media file 112 is not supported by an operating system or data storage facility. In this case, each file of the multiple media files 124 stores a relatively short time period's status information, such as about five minutes' worth of status information. Consequently, one file of the multiple media files 124 may be written to, as messages are received from the medical devices 102-104, and the remaining files of the multiple media files 124 may be read to support playback of the status information to the monitoring stations 120-122.

The media file 112 may be implemented using network digital video recorder (nDVR) technology, such as the Wowza nDVR technology and the Wowza Streaming Engine, both available from Wowza Media Systems, LLC, 523 Park Point Drive, Suite 300, Golden, CO 80401.

Calculating an Index into the Media or Archive File to Information of Interest

As noted, each medical device 102-106 (FIG. 1) sends a stream of status information messages via the computer network 108. Each message may be carried by an individual network packet, or a message may require several network packets to transport the message. The messages and/or the packets may include sequence numbers to facilitate detecting gaps in the message stream. Optionally or alternatively, non-receipt of any message or packet from a given medical device 102-106 for a predetermined period of time may be used to indicate a gap in computer network connectivity.

Figure 10:
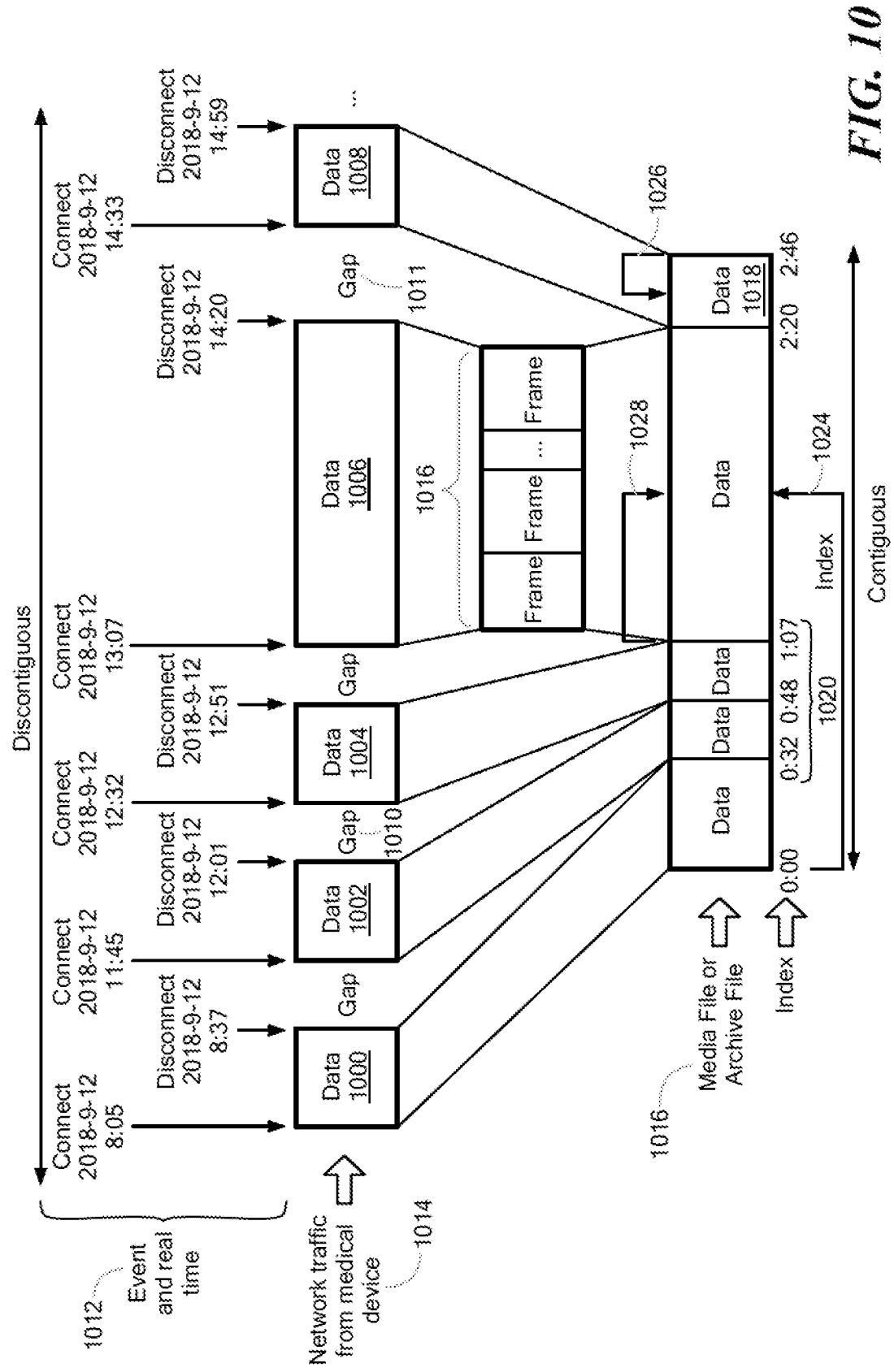
FIG. 10 is a schematic diagram illustrating how non-contiguous status information in messages from medical devices is stored in a contiguous media file, according to an embodiment of the present invention.

The media server 114 (FIG. 1) stores received status information into the data store 110 as the media server 114 receives the status information from the medical devices 102-106. The media server 114 pauses storing status information about a given medical device 102-106 into the data store 110 during each gap in network connectivity with the medical device 102-106, as schematically illustrated in FIG. 10. Hypothetical exemplary times during which status information is received from a given medical device 102-106 are indicated by respective periods of computer network connectivity (data blocks) 1000, 1002, 1004, 1006 and 1008. Gaps in computer network connectivity, such as gaps 1010 and 1011, occur between respective consecutive pairs of the data blocks, such as between data block pair 1002-1004 and between data block pair 1006-1008, from individual ones of the medical devices 102-106.

Although the network packets of a given message from a given medical device 102-106, or the network packets of a sequence of messages from the given medical device 102-106, may arrive spaced apart in time, the time between packets is not considered a gap in network connectivity. Instead, as used herein, a gap in network connectivity prevents receipt of at least one message from a medical device 102-106 and is detectable by the media server 114.

Times at which computer network connectivity begins (connect events) and ends (disconnect events) are indicated at 1012. Collectively, the data blocks 1000-1008 are referred to as network traffic 1014 from the medical device 102-106. The network traffic 1014 is discontiguous, in that the data blocks 1000-1008 do not share any common boundaries. Gaps 1010-1011 occur between adjacent data messages 1000-1008.

Each message 1000-1008 may include one or more video frames, as indicated at 1016. The media server 114 stores the status information in the media file 1018 (112). Thus, status information from consecutive received data blocks, for example data blocks 1002 and 1004, may be stored contiguously, as indicated at 1020, in the data store 1018, even if there is a time gap 1010 between the consecutive received data blocks 1002 and 1004. Consequently, the entire media file 1018 stores data contiguously.

The media file 1018 (112) may be accessed using an index, for example a time index or a frame index, represented by exemplary index 1024. The index 1024 indicates how far from the beginning of the media file 1018 (112) data of interest begins, i.e., the index 1024 is a pointer, relative to the beginning of the media file 1018 (112). Similarly, any of the archive files 113 (FIG. 1) may be accessed using an index 1024. However, in some cases, the index 1026 may indicate how far from the end of the media file 1018 data of interest begins.

As noted, the network connectivity log 116 (FIG. 1) is configured to automatically record: (a) times at which each medical device 102-106 connects to the computer network 108 and (b) times at which each medical device 102-106 disconnects from the computer network 108. FIG. 11 is a schematic diagram illustrating data fields 1100, and hypothetical exemplary contents, of the network connectivity log 116, according to an embodiment of the present invention. The network connectivity log 116 includes one record for each computer network connect event and one record for each computer network disconnect event.

Each record includes: a field 1102 that identifies a medical device, such as by a medical device serial number; a time field 1104 that identifies a time at which the medical device identified in field 1102 experiences an event; an event type field 1106 that indicates whether the corresponding event is a connect event or a disconnect event; and a field 1108 that indicates in which file (media file 112 or one of the archive files 113) status information, for example video frames, from the event is stored.

For simplicity, the hypothetical exemplary contents of the data fields 1100 include information about only one medical device (IC2958). However, information about other medical devices may be interspersed in the network connectivity log 116. That is, records for a variety of medical devices 102-106 may be stored in a single network connectivity log 116.

When a user commands playback of non-live, i.e., recorded, medical device status information, the media server 114 (FIG. 1) automatically ascertains which file, i.e., the media file 112 or one of the archive files 113, contains the desired medical device status information, and the media server 114 calculates the index 1024 or 1026 (FIG. 10), relative to the beginning or end of the appropriate file 1018, where the requested status information is stored. The user may command playback of non-live medical device status information through the web pages 800 and 900 (FIGS. 8 and 9). For example, the user may click on an alert 804 (FIG. 8) or 918 (FIG. 9), select "Previous 5 Hours" 808 or "Archive" 812 (FIG. 8), back up 910 or 912 (FIG. 9) or skip forward 914 or 916 in time, or enter a specific time 908 at which playback is to begin. In response, the media server 114 uses the network connectivity log 116 fields 1100 (FIG. 11) to automatically ascertain which file, i.e., the media file 112 or one of the archive files 113, contains the desired medical device status information. In addition, the media server 114 calculates the index 1024 or 1026 (FIG. 10), relative to the beginning or end of the appropriate file 1018, where the requested status information is stored.

When the user commands playback of non-live medical device status information, the user implicitly or explicitly specifies a time at which the status information of interest was received by the media server 114. For example, each alert in the Alert Summary 804 (FIG. 8) or 918 (FIG. 9) has an associated time. Clicking on an alert causes the web server 118 to use the time of the selected alert. Invoking the "back up 10 seconds" button 910 causes the web server 118 to calculate a time 10 seconds earlier than the time of the currently displayed status information. Similarly, invoking the "skip forward 60 seconds" button 916 causes the web server 118 to calculate a time 60 seconds later than the time of the currently displayed status information. Optionally, the user may enter a specific time 908.

The media server 114 searches the network connectivity log 116 fields 1100 (FIG. 11) for a connect-disconnect event pair (for the specified medical device ID, field 1102) that spans the implicitly or explicitly specified time. If such a connect-disconnect event pair is found, the field 1108 identifies in which file the status information is stored. If no such connect-disconnect event pair is found, no status information for the specified time is available, and an error message may be displayed to the user.

Figure 12:
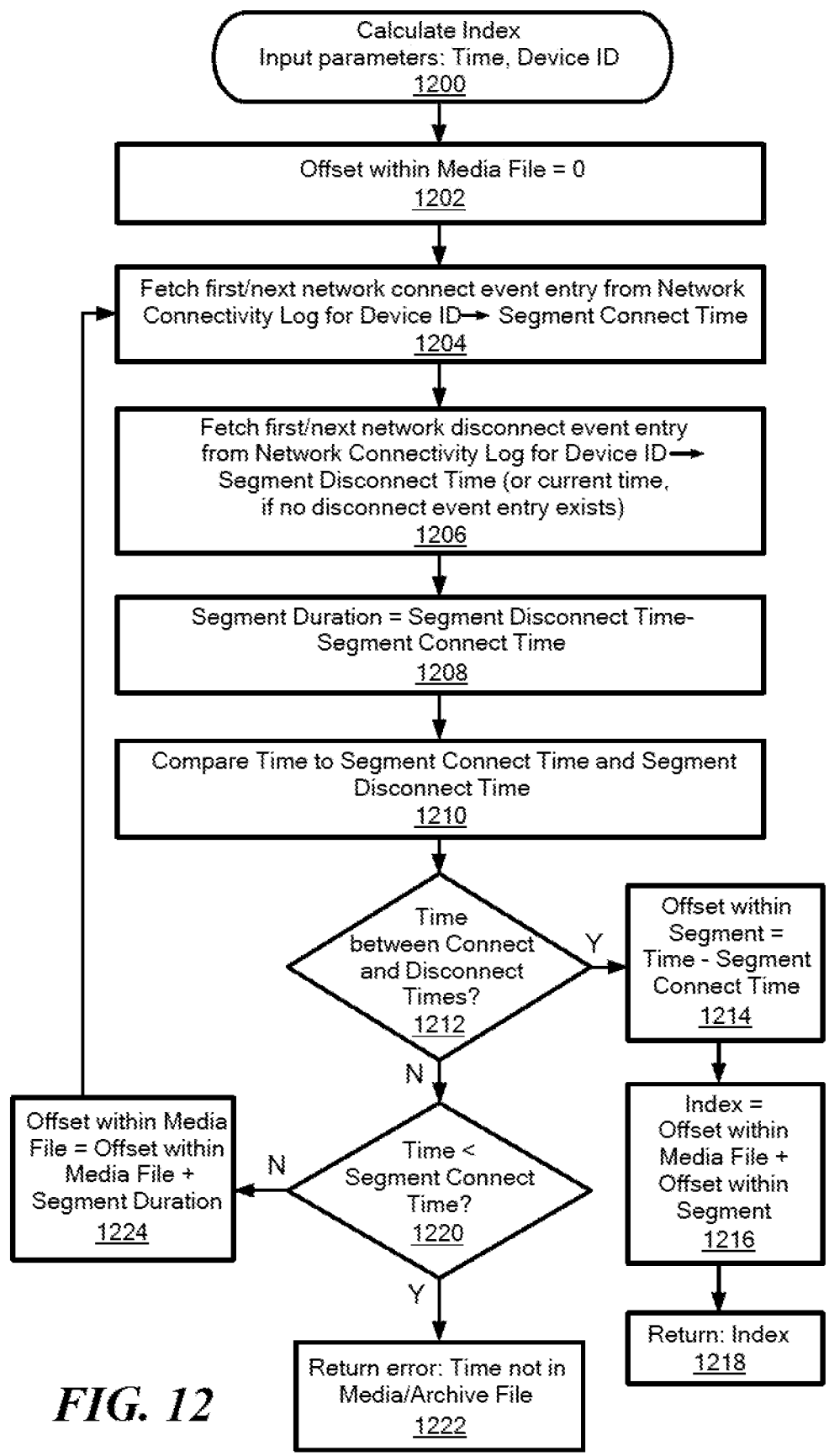
FIG. 12 contains a flowchart schematically illustrating a process by which the media server of the system of FIG. 1 calculates an index into a media file or an archive file to data of interest, according to an embodiment of the present invention.

FIG. 12 contains a flowchart schematically illustrating a process 1200 for calculating the index 1024 (FIG. 10). The process 1200 accepts two input parameters: a time of interest (Time) and a medical device identifier (Device ID), i.e., an identifier of one of the medical devices 102-106. The time of interest (Time) may be a time implicitly or explicitly specified by the user, such as by selecting a particular alert in an Alert Summary 804 or 918 (FIG. 8 or 9), or by clicking the "back up 10 seconds" button 912.

At 1202, an internal variable (Offset within Media File) is initialized to zero, and the process 1200 enters a loop. At the beginning of the loop, at 1204, the first network connect event entry for the specified medical device (Device ID) is fetched from the network connectivity log 116, and the time of the connect event is stored in a temporary variable (Segment Connect Time). At 1206, the first network disconnect event entry for the specified medical device (Device ID) is fetched from the network connectivity log 116, and the time of the disconnect event is stored in a second temporary variable (Segment Disconnect Time). The term "segment" here refers to a period of continuous network connectivity for the specified medical device 102-106.

A duration of the computer network connection (the segment) is calculated by subtracting the Segment Connect Time from the Segment Disconnect Time, and the result of the calculation is stored in a third temporary variable (Segment Duration).

At 1210, the time of interest (Time) is compared to the Segment Connect Time and to the Segment Disconnect Time to ascertain whether the time of interest (Time) is between the Segment Connect Time and the Segment Disconnect Time, i.e., whether the time of interest (Time) occurs during the current segment (period of network connectivity). At 1212, if the time of interest (Time) is between the Segment Connect Time and the Segment Disconnect Time, control passes to 1214. At 1214, another temporary variable (Offset within Segment) is calculated by subtracting Segment Connect Time from the time of interest (Time). The Offset within Segment indicates how far into the current segment (period of network connectivity) the time of interest occurs. A graphic example of a hypothetical Offset within Segment value is shown at 1028 (FIG. 10).

At 1216, a return value (Index) is calculated by adding the Offset within Segment to the Offset within Media File. This return value (Index), which corresponds to the index 1024 exemplified in FIG. 10, is returned at 1218. Control returns to the caller of the procedure 1200.

If, however, at 1212, the time of interest (Time) is not between the Segment Connect Time and the Segment Disconnect Time, control passes to 1220. The time of interest (Time) does not occur during the current segment (period of network connectivity). At 1220, the time of interest (Time) is compared to the Segment Connect Time. If the time of interest (Time) is before, i.e., less than, the Segment Connect Time, the time of interest (Time) occurred before the next segment of network connectivity, i.e., during a gap in network connectivity. Consequently, the media or archive file 112 or 113 does not contain status information for the time of interest (Time). Control passes to 1222, where an error (Time not in Media/Archive File) is returned, and control returns to the caller of the procedure 1200.

On the other hand, at 1220, if the time of interest (Time) is not less than, i.e., not before, the Segment Connect Time, control passes to 1224. A subsequent segment may include the time of interest (Time). The Offset within Media File is increased by the Segment Duration, shifting the Offset within Media File to the beginning of the next segment in the media or archive file. Control returns to the beginning of the loop, i.e., to 1204, where the next network connect event entry is fetched from the network connectivity log 116.

If a monitoring station 120-122 is displaying recent information, such as the "previous 5 hours" web page 900 (FIG. 9), it may be more convenient to use an index 1026 (FIG. 10) relative to the end of a media file 1018, rather than the index 1024 from the beginning of the media file 1018. As new messages arrive from the corresponding medical device 102-106, new status information is added to the end of the media file 1018. Thus, the end of the media file 1018 contains the most recent status information. Typically, a user is interested in the most recent status information, and the user interface controls 910-916 enable the user to back up or skip forward, relative to the displayed information. Thus, calculating the index relative to the end of the media file 1018, rather than relative to the beginning of the media file 1018, may be advantageous, at least in certain circumstances.

The process 1200 may be easily modified to calculate the index relative to the end of the media file 1018. According to this modification, in operation 1214, the Offset within Segment is calculated by subtracting the time of interest (Time) from the Segment Disconnect Time. In operation 1220, the time of interest (Time) is compared to the Segment Disconnect Time. If the time of interest (Time) is greater than, i.e., later than, the Segment Disconnect Time, control passes to 1222, otherwise control passes to 1224.

As used in the claims, "an end of the media file" refers to either the beginning of the media file or the end opposite the beginning of the media file. In other words, an end of the media file refers to either end of the media file.

As noted, when a user commands playback of non-live, i.e., recorded, medical device status information, the web server 118 sends a status request, including a time of interest, to the media server 114 (FIG. 1). In response, the media server 114 automatically ascertains which file, i.e., the media file 112 or one of the archive files 113, contains the desired medical device status information, and the media server 114 calculates the index 1024 or 1026 (FIG. 10), relative to the beginning or end of the appropriate file 1018, where the requested status information is stored. The media server 114 uses the process 1200 of FIG. 12 to calculate the index 1024 or 1026. The media server 114 then fetches stored status information stored in the media file 112 or archive file 113, as the case may be, that begins at the calculated index. The media server 114 provides the fetched status information to the web server 118, and the web server 118 provides the status information to the appropriate client 120 or 122.

Thus, the media server 114 is configured to receive a status request that includes a time at which requested status information was captured. The media server 114 is also configured to access the network connectivity log 116 and calculate the index 1024 (FIG. 10), relative to the beginning or end of the media or archive file 1018, where the requested status information is stored, taking into account the occasional gaps 1010, 1011, etc., in computer network connectivity between the medical device 102-106 and the computer network 108, as represented in the network connectivity log 116. The media server 114 is also configured to request a portion of the stored media file 112 or archive file 113 beginning at the calculated index 1024. The media server 114 is further configured to provide the portion of the stored media file 112 or archive file 113 beginning at the calculated index 1024.

Figure 13:
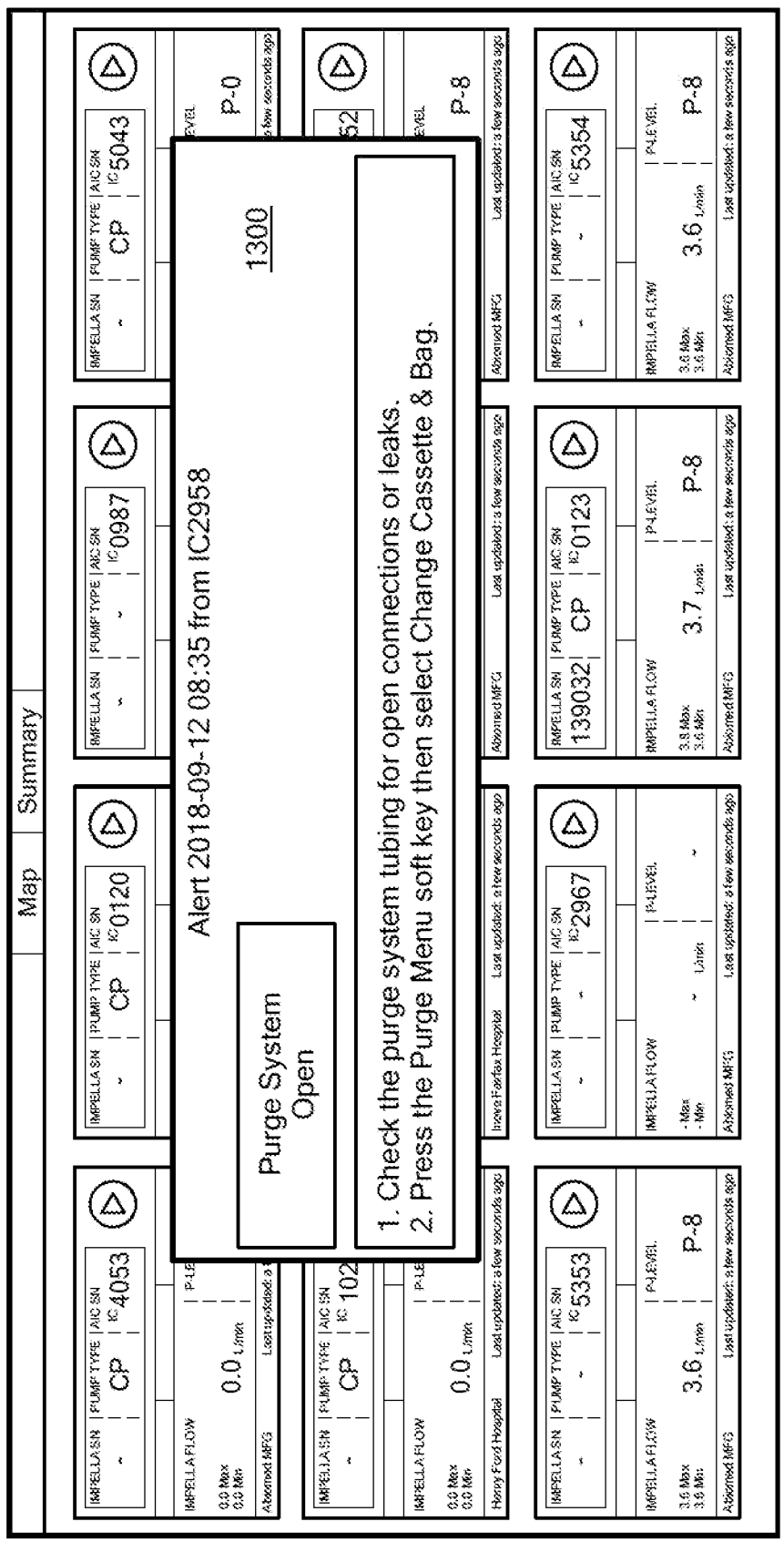
FIG. 13 illustrates an exemplary hypothetical pop-up alert generated by the data storage and retrieval system of FIG. 1, according to an embodiment of the present invention.

Optionally, the web server 118 displays pop-up message, exemplified by a hypothetical pop-up message 1300 in FIG. 13, on one or more of the monitoring stations 120-122 when a new alert is raised. A web application executed in conjunction with the media server 114 and/or the web server 118 may create the pop-up message. The pop-up message may include a clickable link that includes a URL which, if invoked, transfers to a web page similar to the web page of FIG. 9, as though the user clicked on the corresponding alert in region 918 or 804 (FIG. 8).

Figure 14:
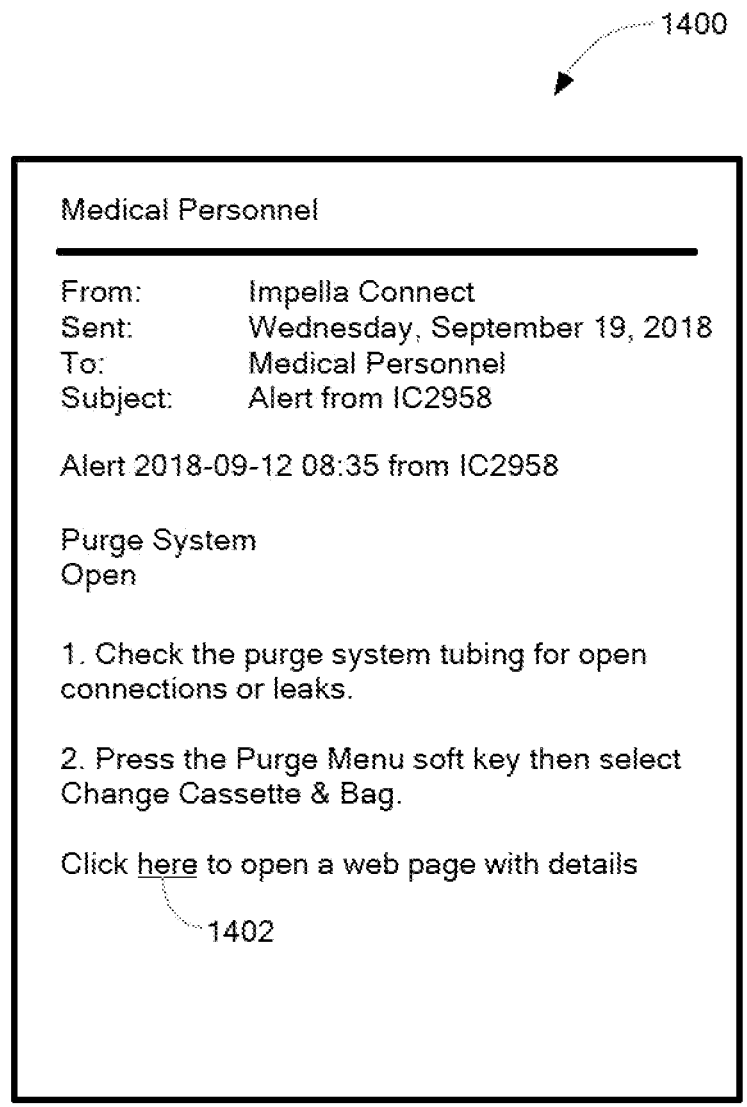
FIG. 14 illustrates an exemplary hypothetical e-mail message containing an alert and link to more information, generated by the data storage and retrieval system of FIG. 1, according to an embodiment of the present invention.

Optionally, an outgoing e-mail server (SMTP server) 126 (FIG. 1) sends an e-mail message to one or more predefined e-mail addresses whenever an alert is raised. FIG. 14 illustrates an exemplary hypothetical e-mail message 1400. The e-mail message 1400 may include information about the alert, as well as a link 1402 that includes a URL which, if invoked, opens a web page similar to the web page of FIG. 9, as though the user clicked on the corresponding alert in region 918 or 804 (FIG. 8).

The media server 114, web server 118 and data store 110 may be implemented by a processor executing instructions stored in a memory. The instructions may include instructions for implementing the process 1200 described with reference to FIG. 12, as well as processes described with reference to FIGS. 1, 7-11, 13 and 14.

The network connectivity log 116 may be implemented with a relational database and may include a front end (load balancer) that distributes access requests across multiple copies of the database to support a high volume of requests. Similarly, the data store 110 may include a front end (load balancer) that distributes load across multiple copies of the media file 112 and/or the archive files 113. The web server 118 and/or the media server 114 may include respective front ends (load balancers) that distribute load across multiple copies of the web server 118 and/or the media server 114.

In some embodiments, one media file 112 stores status information from only one of the medical devices 102-106, i.e., each medical device has an associated media file 112. However, in other embodiments, one media file 112 stores status information from multiple medical devices 102-106. Similarly, one archive file 113 may service one or multiple medical devices 102-106.

While the invention is described through the above-described exemplary embodiments, modifications to, and variations of, the illustrated embodiments may be made without departing from the inventive concepts disclosed herein. For example, although specific parameter values, such as timeouts and recording times, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The media server 114, data store 110, web server 118 and/or network connectivity log 116, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective elements from one another and are not intended to indicate any particular order or total number of elements in any particular embodiment. Thus, for example, a given embodiment may include only a second local variable and a third local variable.

The invention claimed is:

1. A data storage and retrieval system for non-contiguous device data, the system comprising:
a media server connectable to a computer network and configured to automatically:
receive messages from a device via the computer network, wherein the messages contain status information about the device;
store the status information from the received messages into a media file of a data store, wherein the media server stores status information from received messages contiguously, in time order, in the media file with time gaps caused by occasional gaps in connectivity of the computer network between the device and the media server;
receive a status request for status information stored in the media file, wherein the status request includes a status information time at which the requested status information was captured at the device;
access a network connectivity log and calculate a time index, relative to an end of the media file, wherein the network connectivity log includes (a) times at which the device connects to the computer network and (b) times at which the device disconnects from the computer network, and wherein the media server is configured to calculate the time index by: (a) locating a connect-disconnect pair in the network connectivity log that includes the status information time, (b) calculating a first time offset from the end of the media file to an end of a media file segment beginning at the device connect time of the located connect-disconnect pair, (c) calculating a second time offset from the end of the media file segment to the status information time, and (d) combining the first time offset and the second time offset;
request, from the data store via a provisional request, a portion of the media file beginning at the calculated time index; and
provide, in response to the status request, the portion of the media file beginning at the calculated time index returned from the data store.

2. A system according to claim 1, wherein the media server is further configured to automatically cause display of a pop-up message when a message indicates the device requires attention.

3. A system according to claim 2, wherein the pop-up message comprises a URL of a web page that contains additional information about the status of the device.

4. A system according to claim 1, further comprising an outgoing e-mail server configured to send an e-mail message when a message from the device indicates the device requires attention.

5. A system according to claim 4, wherein the e-mail message comprises a URL of a web page that contains additional information about the status of the device.

6. A system according to claim 1, wherein the media file comprises status information for a plurality of different devices.

7. A system according to claim 1, wherein the media file comprises a sequence of video frames.

8. A system according to claim 7, wherein the video frames comprise copies of images displayed on a display of the device.

9. A system according to claim 8, wherein the device is a medical device controller coupled to a blood pump.

10. A system according to claim 8, wherein the media server is further configured to generate an alert based on text extracted from at least one of the video frames.

11. A system according to claim 8, wherein the media server is further configured to identify the device based on text extracted from at least one of the video frames.

12. A system according to claim 1, wherein the media server is further configured to access the network connectivity log and generate an alert when a calculated percentage of the time in which the device is connected to computer network drops below a predetermined threshold.

13. A system according to claim 1, wherein the messages further comprise sequence numbers for detecting when the device disconnects from the computer network.

14. A method for storing and retrieving non-contiguous device data, the method comprising:
receiving, by a media server, messages from a device via a computer network, wherein the messages contain status information about the device;
storing, by the media server, the status information from the received messages into a media file of a data store, wherein the media server stores status information from received messages contiguously, in time order, in the media file with time gaps caused by occasional gaps in connectivity of the computer network between the device and the media server;
receiving, by the media server, a status request for status information stored in the media file, wherein the status request includes a status information time at which the requested status information was captured at the device;
accessing, by the media server, a network connectivity log and calculating a time index, relative to an end of the media file, wherein the network connectivity log includes (a) times at which the device connects to the computer network and (b) times at which the device disconnects from the computer network, and wherein the media server is configured to calculate the time index by: (a) locating a connect-disconnect pair in the network connectivity log that includes the status information time, (b) calculating a first time offset from the end of the media file to an end of a media file segment beginning at the device connect time of the located connect-disconnect pair, (c) calculating a second time offset from the end of the media file segment to the status information time, and (d) combining the first time offset and the second time offset;
requesting, by the media server, from the data store via a provisional request, a portion of the media file beginning at the calculated time index; and
providing, by the media server, in response to the status request, the portion of the media file beginning at the calculated time index returned from the data store.

15. A non-transitory computer-readable medium encoded with instructions that, when executed by the media server, establish processes for performing the method of claim 14.

16. A method according to claim 14, wherein the media file comprises a sequence of video frames.

17. A method according to claim 16, wherein the video frames comprise copies of images displayed on a display of the device.

18. A method for storing and retrieving non-contiguous device data, the method comprising:
   receiving, by a media server, messages from a device via a computer network, wherein the messages contain a plurality of video frames;
   storing, by the media server, the video frames from the received messages into a media file of a data store, wherein the media server stores video frames from received messages contiguously, in time order, in the media file with time gaps caused by occasional gaps in connectivity of the computer network between the device and the media server;
   receiving, by the media server, a status request for video frames stored in the media file, wherein the status request includes a requested frame value;
   accessing, by the media server, a network connectivity log and calculating a frame index, relative to an end of the media file, wherein the network connectivity log includes (a) frame values at which the device connects to the computer network and (b) frame values at which the device disconnects from the computer network, and wherein the media server is configured to calculate the frame index by: (a) locating a connect-disconnect pair in the network connectivity log that includes the requested frame value, (b) calculating a first frame offset from the end of the media file to an end of a media file segment beginning at the device connect time of the located connect-disconnect pair, (c) calculating a second frame offset from the end of the media file segment to the requested frame value, and (d) combining the first frame offset and the second frame offset;
   requesting, by the media server, from the data store via a provisional request, a portion of the media file beginning at the calculated frame index; and
   providing, by the media server, in response to the status request, the portion of the media file beginning at the calculated frame index returned from the data store.

19. A non-transitory computer-readable medium encoded with instructions that, when executed by the media server, establish processes for performing the method of claim 16.

20. A method according to claim 18, wherein the video frames from the received messages comprise copies of images displayed on a display of the device.

* * * * *

UNITED STATES PATENT AND TRADEMARK OFFICE
CERTIFICATE OF CORRECTION

| | | |
|---|---|---|
| PATENT NO. | : 12,183,459 B2 | Page 1 of 1 |
| APPLICATION NO. | : 18/140673 | |
| DATED | : December 31, 2024 | |
| INVENTOR(S) | : Alessandro Simone Agnello and Paul Roland Lemay | |

It is certified that error appears in the above-identified patent and that said Letters Patent is hereby corrected as shown below:

On the Title Page

Item (54) Title and in the Specification Column 1, Lines 1-2 Now reads:
"DATA STORAGE AND RETRIEVAL SYSTEM FOR NON-CONTIGUOUS MEDICAL DEVICE";
Should read:
-- DATA STORAGE AND RETRIEVAL SYSTEM FOR NON-CONTIGUOUS MEDICAL DEVICE OPERATIONAL DATA --.

Signed and Sealed this
Eleventh Day of March, 2025

Coke Morgan Stewart
*Acting Director of the United States Patent and Trademark Office*